United States Patent Office

Plant Pat. 2,074
Patented July 25, 1961

2,074
ROSE PLANT

Bernice Lafayette House, Tyler, Tex., assignor, by mesne assignments, to Armstrong Nurseries, Inc., Ontario, Calif., a corporation of California No Drawing. Filed Oct. 21, 1960, Ser. No. 67,872
1 Claim. (Cl. 47—61)

The present invention relates to a new and distinct variety of rose plant of the climber class, which originated as a bud sport of the variety known as "Circus" (Plant Patent No. 1,382), but which is definitely distinguished from the parent variety by its climbing habit of growth.

This new variety was discovered by me while inspecting the fields where plants of the variety "Circus" were being grown under my direction and control, near Tyler, Texas, said field plants constituting cultivated stock that was being grown on the nursery property of the nursery business in which I was a partner. At the time of my discovery, my attention was attracted to the new variety by the unusually vigorous and climbing habit of a particular plant of the variety "Circus." Upon close examination of this plant, I found that it had sported, and I thereupon promptly took steps to preserve the sport, keep it under observation, and to asexually reproduce the same for the purpose of determining whether its climbing habit was fixed and transmissible by asexual reproduction. As the result, the climbing habit was fully confirmed by asexual reproduction of the original sport as performed by budding the same at both Tyler, Texas, and Ontario, California.

The parent variety "Circus" is a popular variety of the bush type and of the hybrid polyantha class, but so far as I am aware, it has never previously exhibited a climbing habit, and its growth has been that of the average bush rose.

The new variety herein is substantially identical in all respects to its parent, except that it is definitely a climber, as evidenced by its vigorous and strong canes which attain a height at maturity of from 8 to 10 feet. Like most climbing sports of other bush varieties, my new variety is characterized by a habit of producing no flowers on the canes of the current season, but produces profuse blooms in the spring on the growth of the preceding year, and then intermittently flowering from the same wood for the remainder of the growing season. This is a marked contrast with the relatively continuous blooming or ever-blooming habit from current season wood that is characteristic of the bush form of the parent variety "Circus."

In view of the general similarities between my new variety and its parent, except as noted in the foregoing, it is unnecessary to specifically describe or illustrate the new variety in detail herein, since it otherwise substantially conforms to the detailed description and illustration embodied in Plant Patent No. 1,382, granted April 19, 1955, to which reference may be readily had.

I claim:

A new and distinct variety of rose plant of the climber class, substantially as herein shown and described, characterized particularly as to novelty by being substantially identical with its parent variety "Circus" (Plant Patent No. 1,382), but being essentially distinguished therefrom by its vigorous and climbing habit of growth, as evidenced by its strong canes which attain a mature height of from 8 to 10 feet, and the habit of producing no flowers on current season's canes, while producing profuse blooms in the spring on the growth of the preceding year and then intermittently flowering from the same wood during the remainder of the growing season.

No references cited.